(12) United States Patent
Lehmann-Lintz et al.

(10) Patent No.: US 6,617,325 B1
(45) Date of Patent: Sep. 9, 2003

(54) BIPHENYL DERIVATIVES, PRODUCTION THEREOF AND USES AS MEDICINES

(75) Inventors: Thorsten Lehmann-Lintz, Ochsenhausen/Laubach (DE); Armin Heckel, Biberach (DE); Leo Thomas, Biberach (DE); Michael Mark, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/031,585

(22) PCT Filed: Jul. 15, 2000

(86) PCT No.: PCT/EP00/06770

§ 371 (c)(1),
(2), (4) Date: May 15, 2002

(87) PCT Pub. No.: WO01/05762

PCT Pub. Date: Jan. 25, 2001

(30) Foreign Application Priority Data

Jul. 20, 1999 (DE) .......................... 199 33 926

(51) Int. Cl.$^7$ .................. A01N 43/66; A01N 43/40; C07D 237/28; C07D 213/02; C07D 211/92
(52) U.S. Cl. .................. 514/241; 514/243; 514/248; 514/252.03; 514/252.14; 514/258.1; 514/266.22; 514/318; 514/319; 514/330; 544/180; 544/183; 544/215; 544/235; 544/238; 544/284; 546/194; 546/196; 546/198; 546/199; 546/200; 546/201; 546/202; 546/207; 546/208; 546/209; 546/210; 546/213; 546/214; 546/224
(58) Field of Search .................. 546/224, 194, 546/196, 198, 199, 200, 201, 202, 207, 208, 209, 210, 213, 214; 514/330, 241, 243, 258, 252.03, 252.14, 258.1, 266.22, 318, 319; 544/180, 183, 215, 255, 238, 284

(56) References Cited

U.S. PATENT DOCUMENTS 5,028,616 A * 7/1991 Desai et al. ............... 514/321
5,750,540 A * 5/1998 Tsuchiya et al. .......... 514/318

FOREIGN PATENT DOCUMENTS

EP 0 887 345 A 12/1998
WO WO 99 63929 A 12/1999

\* cited by examiner

*Primary Examiner*—Alan L. Rotman
*Assistant Examiner*—Raymond Covington
(74) *Attorney, Agent, or Firm*—Robert P. Raymond; Philip I. Datlow; Alan R. Stempel

(57) ABSTRACT

The present invention relates to biphenyl derivatives of general formula

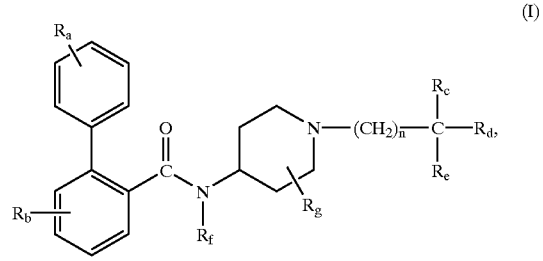

(I)

wherein $R_a$ to $R_g$ and n are defined as in claim 1, the isomers and salts thereof, particularly the physiologically acceptable salts thereof, which are valuable inhibitors of the microsomal triglyceride-transfer protein (MTP), medicaments containing these compounds and their use, as well as the preparation thereof.

8 Claims, No Drawings

BIPHENYL DERIVATIVES, PRODUCTION THEREOF AND USES AS MEDICINES

The present invention relates to biphenyl derivatives of general formula

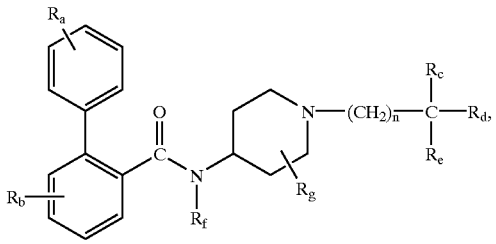

(I)

their isomers, their salts, particularly the physiologically acceptable salts thereof which have valuable pharmacological properties.

The compounds of the above general formula I are valuable inhibitors of the microsomal triglyceride-transfer protein (MTP) and are therefore suitable for lowering the plasma level of the atherogenic lipoproteins.

In the above general formula I n denotes the number 1, 2, 3, 4 or 5, $R_a$ and $R_b$, which may be identical or different, each denote a hydrogen, fluorine, chlorine or bromine atom, a $C_{1-3}$-alkyl group wherein the hydrogen atoms may be wholly or partially replaced by fluorine atoms, a hydroxy, $C_{1-3}$-alkoxy, amino, $C_{1-3}$-alkylamino or di-($C_{1-3}$-alkyl)-amino group, $R_c$ denotes a hydrogen atom, a $C_{1-10}$-alkyl, $C_{3-7}$-cycloalkyl or $C_{3-7}$-cycloalkyl-$C_{1-3}$-alkyl group, wherein in each case the hydrogen atoms may be wholly or partially replaced by fluorine atoms, a phenyl, naphthyl or monocyclic 5 or 6-membered heteroaryl group optionally substituted by a fluorine, chlorine or bromine atom, by a $C_{1-3}$-alkyl group wherein the hydrogen atoms may be wholly or partially replaced by fluorine atoms, by a hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, by a 3- to 7-membered cycloalkyleneimino group, wherein the methylene group in the 4 position in a 6- or 7-membered cycloalkyleneimino group may additionally be replaced by an oxygen or sulphur atom, by a sulphinyl, sulphonyl, imino or N-($C_{1-3}$-alkyl)-imino group, by a nitro, amino, $C_{1-3}$-alkylamino, di-($C_{1-3}$-alkyl)-amino, $C_{1-3}$-alkylcarbonylamino, N-($C_{1-3}$-alkyl)-$C_{1-3}$-alkylcarbonylamino, $C_{1-3}$-alkylsulphonylamino or N-($C_{1-3}$-alkyl)-$C_{1-3}$-alkylsulphonylamino group, wherein the 6-membered heteroaryl group contains one, two or three nitrogen atoms and the 5-membered heteroaryl group contains an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and moreover a phenyl ring may be fused to the abovementioned monocyclic heterocyclic groups via two adjacent carbon atoms, $R_d$ denotes a phenyl, naphthyl or monocyclic 5 or 6-membered heteroaryl group optionally substituted by a fluorine, chlorine or bromine atom, by a $C_{1-3}$-alkyl group wherein the hydrogen atoms may be wholly or partially replaced by fluorine atoms, by a hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, by a 3- to 7-membered cycloalkyleneimino group, wherein the methylene group may additionally be replaced in the 4 position in a 6-or 7-membered cycloalkyleneimino group by an oxygen or sulphur atom, by a sulphinyl, sulphonyl, imino or N-($C_{1-3}$-alkyl)-imino group, by a nitro, amino, $C_{1-3}$-alkylamino, di-($C_{1-3}$-alkyl)-amino, $C_{1-3}$-alkylcarbonylamino, N-($C_{1-3}$-alkyl)-$C_{1-3}$-alkylcarbonylamino, $C_{1-3}$-alkylsulphonylamino or N-($C_{1-3}$-alkyl)-$C_{1-3}$-alkylsulphonylamino group, wherein the 6-membered heteroaryl group contains one, two or three nitrogen atoms and the 5-membered heteroaryl group contains an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and moreover a phenyl ring may be fused to the abovementioned monocyclic heterocyclic groups via two adjacent carbon atoms, $R_e$ denotes a carboxy group, a $C_{1-6}$-alkoxycarbonyl or $C_{3-7}$-cycloalkoxycarbonyl group wherein the alkyl or cycloalkyl moiety may be substituted in each case from the 2 position, relative to the oxygen atom, by a $C_{1-3}$-alkoxy, amino, $C_{1-3}$-alkylamino or di-($C_{1-3}$-alkyl)-amino group, a phenyl-$C_{1-3}$-alkoxycarbonyl or heteroaryl-$C_{1-3}$-alkoxycarbonyl group, while the heteroaryl moiety is as hereinbefore defined, $R_f$ denotes a hydrogen atom, a $C_{1-3}$-alkyl or phenyl-$C_{1-3}$-alkyl group and $R_g$ denotes a hydrogen atom or a $C_{1-3}$-alkyl group.

However, preferred compounds of the above general formula I are those wherein $R_b$ to $R_g$ are as hereinbefore defined and $R_a$ is in the 3' or 4' position and has the meanings given hereinbefore with the exception of the hydrogen atom, the isomers and salts thereof.

However, particularly preferred compounds of the above general formula I are those wherein n denotes the number 3, 4 or 5, $R_a$ denotes a hydrogen, fluorine, chlorine or bromine atom, a $C_{1-3}$-alkyl, trifluoromethyl or $C_{1-3}$-alkoxy group, $R_b$ denotes a hydrogen, fluorine, chlorine or bromine atom, $R_c$ denotes a $C_{1-5}$-alkyl, $C_{3-7}$-cycloalkyl or $C_{3-7}$-cycloalkyl-$C_{1-3}$-alkyl group or a phenyl group optionally substituted by a fluorine, chlorine or bromine atom or by a $C_{1-3}$-alkyl group, $R_d$ denotes a phenyl group optionally substituted by a fluorine, chlorine or bromine atom or by a $C_{1-3}$-alkyl group, $R_e$ denotes a carboxy group, a $C_{1-6}$-alkoxycarbonyl or $C_{3-7}$-cycloalkoxycarbonyl group wherein the alkyl or cycloalkyl moiety may be substituted in each case from the 2 position, relative to the oxygen atom, by a $C_{1-3}$-alkoxy, amino, $C_{1-3}$-alkylamino or di-($C_{1-3}$-alkyl)-amino group, a phenyl-$C_{1-3}$-alkoxycarbonyl, pyridyl-$C_{1-3}$-alkoxycarbonyl or pyrimidyl-$C_{1-3}$-alkoxycarbonyl group, $R_f$ denotes a hydrogen atom or a $C_{1-3}$-alkyl group and $R_g$ denotes a hydrogen atom or a $C_{1-3}$-alkyl group, the isomers and salts thereof.

The following are mentioned as examples of particularly valuable compounds:

(a) methyl 2-methyl-2-phenyl-5-{4-[(4'-trifluoromethyl-biphenyl-2-carbonyl)-amino]-piperidin-1-yl}-pentanecarboxylate, (b) methyl 2-ethyl-2-phenyl-5-{4-[(4'-trifluoromethyl-biphenyl-2-carbonyl)-amino]-piperidin-1-yl}-pentanecarboxylate and (c) methyl 2-methyl-2-phenyl-6-{4-[(4'-trifluoromethyl-biphenyl-2-carbonyl)-amino]-piperidin-1-yl}-hexanecarboxylate.

According to the invention, the new compounds are obtained by methods known from the literature, for example by the following methods:

a. reacting a compound of general formula

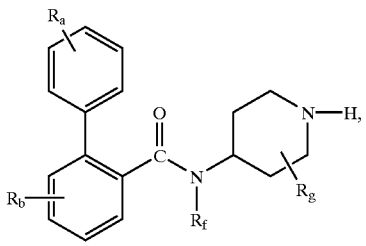
(II)

wherein $R_a$, $R_b$, $R_f$ and $R_g$ are as hereinbefore defined, with a compound of general formula

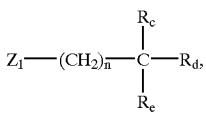
(III)

wherein n and $R_c$ to $R_e$ are as hereinbefore defined and $Z_1$ denotes a nucleofugic leaving group such as a halogen atom, e.g. a chlorine, bromine or iodine atom, or a p-nitrophenyl group.

The reaction is preferably carried out in a solvent such as methylene chloride, acetonitrile, tetrahydrofuran, toluene, acetone/water, dimethylformamide or dimethylsulphoxide optionally in the presence of a base such as sodium hydride, potassium carbonate, potassium tert-butoxide or N-ethyl-diisopropylamine at temperatures between 0 and 100° C., preferably at temperatures between 10 and 60° C.

b. In order to prepare a compound of general formula I, wherein $R_e$ has the meanings given hereinbefore for $R_e$ with the exception of the carboxy group:

esterifying a compound of general formula

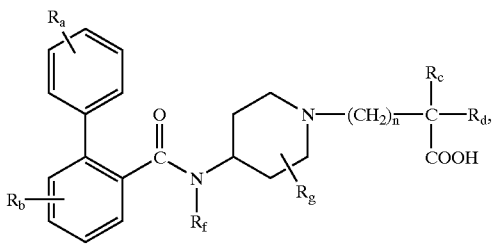
(IV)

wherein n, $R_a$ to $R_d$, $R_f$ and $R_g$ are as hereinbefore defined, or the reactive derivatives thereof with an alcohol of general formula

(V)

wherein $R_e'$ denotes a $C_{1-6}$-alkoxy or $C_{3-7}$-cycloalkoxy group wherein the alkyl or cycloalkyl moiety may be substituted in each case from the 2 position, relative to the oxygen atom, by a $C_{1-3}$-alkoxy, amino, $C_{1-3}$-alkylamino or di-($C_{1-3}$-alkyl)-amino group, a phenyl-$C_{1-3}$-alkoxy or heteroaryl-$C_{1-3}$-alkoxy group, while the heteroaryl moiety is as hereinbefore defined, or, in order to prepare a tert-butyl ester, 2,2-dimethyl-ethene, in the presence of an acid.

The reaction is optionally carried out in the presence of a solvent or mixture of solvents such as methylene chloride, dimethylformamide, benzene, toluene, chlorobenzene, tetrahydrofuran, benzene/tetrahydrofuran or dioxane, but preferably in an excess of the alcohol of general formula V used as solvent, optionally in the presence of an acid such as hydrochloric acid or sulphuric acid or in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexyl-carbodiimide, N,N'-dicyclohexylcarbodiimide/N-hydroxy-succinimide, N,N'-dicyclohexylcarbodiimide/1-hydroxy-benzotriazole, 2-(1 H-benzotriazol-1-yl)-1,1,3,3-tetramethyluronium-tetrafluoroborate, 2-(1 H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, appropriately at temperatures between 0 and 150° C., preferably at temperatures between 0 and 100° C.

The reaction of a corresponding reactive compound of general formula IV such as the esters, imidazolides or halides with an alcohol of general formula V is preferably carried out in a corresponding alcohol as solvent, optionally in the presence of another solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

The formation of the tert.butyl ester with 2,2-dimethyl-ethene is preferably carried out in a solvent such as diethyl ether, dioxane, methylene chloride or tert.butanol in the presence of an acid such as sulphuric acid, hydrochloric acid or boron fluoride-diethyletherate at temperatures between −20 and 150° C., preferably at temperatures between 0 and 100° C.

c. In order to prepare a compound of general formula I wherein $R_e$ denotes a carboxy group:

converting a compound of general formula

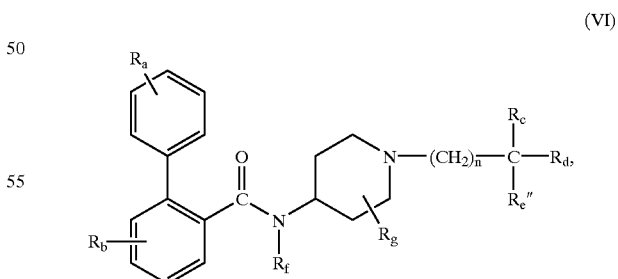
(VI)

wherein n, $R_a$ to $R_d$, $R_f$ and $R_g$ are as hereinbefore defined and $R_e''$ denotes a group which can be converted into a carboxy group, into a compound of general formula I wherein $R_e$ denotes a carboxy group.

The group which may be converted into a carboxy group may be, for example, a carboxyl group protected by a protecting group, such as the functional derivatives thereof, e.g. the unsubstituted or substituted amides, esters, thioesters, trimethylsilyl esters, orthoesters or iminoesters thereof, which may expediently be converted by hydrolysis into a carboxyl group, the esters thereof with tertiary alcohols, e.g. the tert. butyl ester, which are expediently converted into a carboxyl group by treating with an acid or thermolysis, and the esters thereof with aralkanols, e.g. the benzyl ester, which are expediently converted into a carboxyl group by hydrogenolysis.

The hydrolysis is expediently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

If $R_e''$ in a compound of formula VI denotes the tert. butyloxycarbonyl group, for example, this may also be cleaved by treating with an acid such as trifluoroacetic acid, formic acid, p-toluenesulphonic acid, sulphuric acid, hydrochloric acid, phosphoric acid or polyphosphoric acid optionally in an inert solvent such as methylene chloride, chloroform, benzene, toluene, diethyl ether, tetrahydrofuran or dioxane preferably at temperatures between −10 and 120° C., e.g. at temperatures between 0 and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid preferably at the boiling temperature of the solvent used, e.g. at temperatures between 40 and 120° C.

If $R_e''$ in a compound of formula VI denotes the benzyloxycarbonyl group, for example, this may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, and at a hydrogen pressure of 1 to 5 bar.

If according to the invention a compound of general formula I is obtained which contains a nitro group it may be converted by reduction into a corresponding amino compound, or if a compound of general formula I is obtained wherein $R_f$ denotes a hydrogen atom, it may be converted by alkylation into a corresponding compound wherein $R_f$ denotes a $C_{1-3}$-alkyl or phenyl-$C_{1-3}$-alkyl group.

The subsequent reduction of a nitro group is expediently carried out hydrogenolytically, e.g. with hydrogen in the presence of a catalyst such as platinum, palladium/charcoal or Raney nickel in a suitable solvent such as methanol, ethanol, ethyl acetate, tetrahydrofuran, dioxane, dimethylformamide or glacial acetic acid, optionally with the addition of an acid such as hydrochloric acid and at a hydrogen pressure of 1 to 7 bar, but preferably 1 to 5 bar, with metals such as iron, tin or zinc in the presence of an acid such as acetic acid or hydrochloric acid, with salts such as iron(II) sulphate, tin (II) chloride, sodium sulphide, sodium hydrogen sulphite or sodium dithionite, or with hydrazine in the presence of Raney nickel at temperatures between 0 and 100° C., but preferably at temperatures between 20 and 60° C.

The subsequent alkylation is optionally carried out in a solvent or mixture of solvents such as methylene chloride, dimethylformamide, benzene, toluene, chlorobenzene, tetrahydrofuran, benzene/tetrahydrofuran, dioxane, dimethylsulphoxide or sulpholane with an alkylating agent such as a corresponding halide or sulphonic acid ester, e.g. with methyl iodide, ethyl bromide, dimethyl sulphate or benzyl chloride, optionally in the presence of a tertiary organic base or in the presence of an inorganic base, conveniently at temperatures between 0 and 150° C., preferably at temperatures between 0 and 100° C., or by reductive alkylation.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, tert.butyl-dimethylsilyl, acetyl, benzoyl, methyl, ethyl, tert.butyl, trityl, benzyl or tetrahydropyranyl group, a protecting group for a carboxyl group may be a trimethylsilyl, methyl, ethyl, tert.butyl, benzyl or tetrahydropyranyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C. However, a silyl group may also be cleaved using tetrabutylammonium fluoride as described hereinbefore.

However, a benzyl, methoxybenzyl or benzyloxycarbonyl group is cleaved for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain an acidic group such as a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to VI used as starting materials are known from the literature in some cases or may be obtained by methods known from the literature or are described in the Examples. Thus, for example, a compound of general formula III is obtained by esterifying a corresponding disubstituted carboxylic acid and subsequently reacting with an $\alpha,\omega$-dihaloalkane in the presence of a strong base such as lithium diisopropylamide, sodium amide or sodium hydride.

As already mentioned hereinbefore, the compounds of general formula I and the physiologically acceptable salts thereof have valuable pharmacological properties. In particular, they are valuable inhibitors of the microsomal triglyceride-transfer protein (MTP) and are therefore suitable for lowering the plasma levels of the atherogenic lipoproteins.

For example, the compounds according to the invention were investigated for their biological effects as follows:

Inhibitors of MTP were identified by a commercially obtainable MTP activity kit(WAK-Chemie Medical GmbH, Sulzbacherstrasse 15-21, D-65812 Bad Soden, Germany). This test kit contains donor and acceptor particles. The donor particles contain fluorescence-labelled triglycerides in a concentration high enough to cause self-extinction of the fluorescence. When the donor and acceptor particles were incubated with an MTP source, fluorescence-labelled triglycerides were transferred from the donor to the acceptor particles. This led to an increase in the fluorescence in the sample. Solubilised liver microsomes from various species (e.g. rat) could be used as the MTP source. Inhibitors of MTP were identified as the substances which reduced the transfer of fluorescence-labelled triglycerides compared with a control mixture with no inhibitor.

In view of the abovementioned biological properties the compounds of general formula I and the physiologically acceptable salts thereof are particularly suitable for lowering the plasma concentration of atherogenic apolipoprotein B (apoB)-containing lipoproteins such as chylomicrons and/or very low density lipoproteins (VLDL) as well as the residues thereof such as low density lipoproteins (LDL) and/or lipoprotein(a) (Lp(a)), for treating hyperlipidaemias, for preventing and treating atherosclerosis and the clinical sequelae thereof, and for preventing and treating related disorders such as diabetes mellitus, adiposity and pancreatitis, oral administration being preferred.

The daily dose needed to achieve such an effect is between 0.5 and 500 mg, expediently between 1 and 350 mg, but preferably between 5 and 200 mg, in adults.

For this purpose, the compounds of formula I prepared according to the invention, optionally combined with other active substances such as other lipid-lowering agents, for example HMG-CoA-reductase inhibitors, cholesterol biosynthesis inhibitors such as squalene synthase inhibitors and squalene cyclase inhibitors, bile acid-binding resins, fibrates, cholesterol resorption inhibitors, niacin, probucol, CETP inhibitors and ACAT inhibitors may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples which follow are intended to illustrate the invention in more detail:

EXAMPLE 1

Methyl 2-methyl-2-phenyl-5-{4-[(4'-trifluoromethyl-biphenyl-2-carbonyl)-amino]-piperidin-1-yl}-pentanecarboxylate a. methyl 2-phenylpropionate 50 g (0.3 mol) of 2-phenylpropionic acid are dissolved in 375 ml of methanolic hydrochloric acid and stirred for 14 hours at ambient temperature. The solvent is removed and the residue extracted with ethyl acetate and saturated sodium hydrogen carbonate solution. The organic phases are extracted with water and saturated saline solution, dried over magnesium sulphate and concentrated by evaporation.

Yield: 51 g (94.8% of theory).

b. methyl 5-bromo-2-methyl-2-phenyl-pentanecarboxylate 15 g (0.234 mol) of n-butyl lithium as a 2.5 molar solution in hexane are added dropwise to a solution of 32.8 ml (0.234 mol) of diisopropylamine in 200 ml of anhydrous tetrahydrofuran at −30° C. and stirred for 10 minutes at −10° C. 38.4 g (0.234 mol) of methyl 2-phenylpropionate are added dropwise at −76° C. and stirred for 30 minutes at this temperature. Then 26.3 ml (0.257 mol) of 1,3-dibromopropane are added, when the addition has ended the cooling bath is removed and the mixture is stirred for 14 hours at ambient temperature. The reaction solution is poured onto 1.2 l of water and extracted with diethylether. The organic phases are extracted with water, dried over sodium sulphate and the solvent is removed. The residue is distilled under high vacuum.

Yield: 42.7 g (64% of theory), Boiling point: 113–118° C. at 0.2 mmbar c. 4'-trifluoromethyl-biphenyl-2-carboxylic acid chloride 170 ml of oxalyl chloride are added dropwise at 0° C. to a suspension of 30 g (0.113 mol) of 4'-trifluoromethyl-biphenyl-2-carboxylic acid in 500 ml of dichloromethane and 0.2 ml of dimethylformamide. After the reaction has ended the reaction mixture is concentrated by distillation and the 4'-trifluoromethyl-biphenyl-2-carboxylic acid chloride is further reacted as a crude product.

Yield: 32.16 g (100% of theory).

d. 4'-trifluoromethyl-biphenyl-2-carboxylic acid-(1-benzyl-piperidin-4-yl)-amide 34.1 g (0.12 mol) of 4'-trifluoromethyl-biphenyl-2-carboxylic acid chloride, dissolved in 300 ml of dichloromethane, are added dropwise at 15 to 20° C. to a solution of 22.43 ml (0.11 mol) of 4-amino-1-benzyl-piperidine and 42.97 ml (0.31 mol) of triethylamine in 600 ml of dichloromethane. The mixture is stirred for 14 hours at ambient temperature. The reaction solution is diluted with 300 ml of dichloromethane and extracted with a mixture of 1N sodium hydrogen carbonate solution and 1N sodium hydroxide solution. The organic phase is dried over sodium sulphate and the solvent is eliminated. The residue is recrystallised from 650 ml ethanol.

Yield: 31.6 g (65.5% of theory), Melting point: 193° C. $C_{26}H_{25}F_3N_2O$ (M=438.50) Calc.: molar peak $(M+H)^+$=439 Found: molar peak $(M+H)^+$=439 e. 4'-trifluoromethyl-biphenyl-2-carboxylic acid-piperidin-4-yl-amide 31.6 g (0.072 mol) of 4'-trifluoromethyl-biphenyl-2-carboxylic acid-(1-benzyl-piperidin-4-yl)-amide are dissolved in 180 ml ethanol and 180 ml methanol, mixed with 84 ml (0.83 mol) of cyclohexene and 6.53 g of palladium hydroxide (20% on charcoal) and refluxed for four hours. The hot reaction mixture is filtered through kieselguhr and the reaction mixture is concentrated by rotary evaporation.

Yield: 18.5 g (73.7% of theory), $C_{19}H_{19}F_3N_2O$ (M=348.37) Calc.: molar peak $(M+H)^+$=349 Found: molar peak $(M+H)^+$=349 f. methyl 2-methyl-2-phenyl-5-{4-[(4'-trifluoromethyl-biphenyl-2-carbonyl)-amino]-piperidin-1-yl}-pentanecarboxylate 0.611 g (1.75 mmol) of 4'-trifluoromethyl-biphenyl-2-carboxylic acid-piperidin-4-yl-amide, 0.5 g (1.75 mmol) of methyl 5-bromo-2-methyl-2-phenyl-pentanecarboxylate and 0.8 g (5.7 mmol) of potassium carbonate are dissolved in 50 ml dimethylformamide and mixed with water. The mixture is stirred for 72 hours at 90° C. Then the reaction mixture is poured onto water, the precipitate is filtered off and dried. After column chromatography on silica gel (eluant: ethyl acetate) colourless crystals are left.

Yield: 0.15 g (15.5% of theory), $C_{32}H_{35}F_3N_2O_3$ (M=552.64) Melting point: 139–140° C. Calc.: molar peak $(M+H)^+$=553 Found: molar peak $(M+H)^+$=553

The following compounds may be prepared analogously to Example 1:

(1) ethyl 2-methyl-2-phenyl-5-{4-[(4'-trifluoromethyl-biphenyl-2-carbonyl)-amino]-piperidin-1-yl}-pentanecarboxylate (2) propyl 2-methyl-2-phenyl-5-{4-[(4'-trifluoromethyl-biphenyl-2-carbonyl)-amino]-piperidin-1-yl}-pentanecarboxylate (3) butyl 2-methyl-2-phenyl-5-{4-[(4'-trifluoromethyl-biphenyl-2-carbonyl)-amino]-piperidin-1-yl}-pentanecarboxylate (4) pentyl 2-methyl-2-phenyl-5-{4-[(4'-trifluoromethyl-biphenyl-2-carbonyl)-amino]-piperidin-1-yl}-pentanecarboxylate (5) hexyl 2-methyl-2-phenyl-5-{4-[(4'-trifluoromethyl-biphenyl-2-carbonyl)-amino]-piperidin-1-yl}-pentanecarboxylate (6) isopropyl 2-methyl-2-phenyl-5-{4-[(4'-trifluoromethyl-biphenyl-2-carbonyl)-amino]-piperidin-1-yl}-pentanecarboxylate (7) tert.butyl 2-methyl-2-phenyl-5-{4-[(4'-trifluoromethyl-biphenyl-2-carbonyl)-amino]-piperidin-1-yl}-pentanecarboxylate (8) isobutyl 2-methyl-2-phenyl-5-{4-[(4'-trifluoromethyl-biphenyl-2-carbonyl)-amino]-piperidin-1-yl}-pentanecarboxylate (9) sec.butyl 2-methyl-2-phenyl-5-{4-[(4'-trifluoromethyl-biphenyl-2-carbonyl)-amino]-piperidin-1-yl}-pentanecarboxylate

(10) cyclopropyl 2-methyl-2-phenyl-5-{4-[(4'-trifluoromethyl-biphenyl-2-carbonyl)-amino]-piperidin-1-yl}-pentanecarboxylate

(11) cyclobutyl 2-methyl-2-phenyl-5-{4-[(4'-trifluoromethyl-biphenyl-2-carbonyl)-amino]-piperidin-1-yl}-pentanecarboxylate

(12) cyclopentyl 2-methyl-2-phenyl-5-{4-[(4'-trifluoromethyl-biphenyl-2-carbonyl)-amino]-piperidin-1-yl}-pentanecarboxylate

(13) cyclohexyl 2-methyl-2-phenyl-5-{4-[(4'-trifluoromethyl-biphenyl-2-carbonyl)-amino]-piperidin-1-yl}-pentanecarboxylate

(14) cycloheptyl 2-methyl-2-phenyl-5-{4-[(4'-trifluoromethyl-biphenyl-2-carbonyl)-amino]-piperidin-1-yl}-pentanecarboxylate

(15) 2-hydroxyethyl 2-methyl-2-phenyl-5-{4-[(4'-trifluoromethyl-biphenyl-2-carbonyl)-amino]-piperidin-1-yl}-pentanecarboxylate

(16) 3-hydroxypropyl 2-methyl-2-phenyl-5-{4-[(4'-trifluoromethyl-biphenyl-2-carbonyl)-amino]-piperidin-1-yl}-pentanecarboxylate

(17) 2-methoxyethyl 2-methyl-2-phenyl-5-{4-[(4'-trifluoromethyl-biphenyl-2-carbonyl)-amino]-piperidin-1-yl}-pentanecarboxylate

(18) 2-ethoxy-ethyl 2-methyl-2-phenyl-5-{4-[(4'-trifluoromethyl-biphenyl-2-carbonyl)-amino]-piperidin-1-yl}-pentanecarboxylate

(19) 3-methoxypropyl 2-methyl-2-phenyl-5-{4-[(4'-trifluoromethyl-biphenyl-2-carbonyl)-amino]-piperidin-1-yl}-pentanecarboxylate

(20) 3-ethoxy-propyl 2-methyl-2-phenyl-5-{4-[(4'-trifluoromethyl-biphenyl-2-carbonyl)-amino]-piperidin-1-yl}-pentanecarboxylate

(21) 2-amino-ethyl 2-methyl-2-phenyl-5-{4-[(4'-trifluoromethyl-biphenyl-2-carbonyl)-amino]-piperidin-1-yl}-pentanecarboxylate

(22) 3-amino-propyl 2-methyl-2-phenyl-5-{4-[(4'-trifluoromethyl-biphenyl-2-carbonyl)-amino]-piperidin-1-yl}-pentanecarboxylate

(23) 2-methylaminoethyl 2-methyl-2-phenyl-5-{4-[(4'-trifluoromethyl-biphenyl-2-carbonyl)-amino]-piperidin-1-yl}-pentanecarboxylate

(24) 3-methylaminopropyl 2-methyl-2-phenyl-5-{4-[(4'-trifluoromethyl-biphenyl-2-carbonyl)-amino]-piperidin-1-yl}-pentanecarboxylate

(25) 2-dimethylaminoethyl 2-methyl-2-phenyl-5-{4-[(4'-trifluoromethyl-biphenyl-2-carbonyl)-amino]-piperidin-1-yl}-pentanecarboxylate

(26) 3-dimethylaminopropyl 2-methyl-2-phenyl-5-{4-[(4'-trifluoromethyl-biphenyl-2-carbonyl)-amino]-piperidin-1-yl}-pentanecarboxylate

(27) benzyl 2-methyl-2-phenyl-5-{4-[(4'-trifluoromethyl-biphenyl-2-carbonyl)-amino]-piperidin-1-yl}-pentanecarboxylate

(28) pyridin-2-yl-methyl 2-methyl-2-phenyl-5-{4-[(4'-trifluoromethyl-biphenyl-2-carbonyl)-amino]-piperidin-1-yl}-pentanecarboxylate

(29) pyridin-3-yl-methyl 2-methyl-2-phenyl-5-{4-[(4'-trifluoromethyl-biphenyl-2-carbonyl)-amino]-piperidin-1-yl}-pentanecarboxylate

(30) pyridin-4-yl-methyl 2-methyl-2-phenyl-5-{4-[(4'-trifluoromethyl-biphenyl-2-carbonyl)-amino]-piperidin-1-yl}-pentanecarboxylate

(31) pyrimidin-4-yl-methyl 2-methyl-2-phenyl-5-{4-[(4'-trifluoromethyl-biphenyl-2-carbonyl)-amino]-piperidin-1-yl}-pentanecarboxylate

(32) methyl 2-methyl-2-(4-fluoro-phenyl)-5-{4-[(4'-trifluoromethyl-biphenyl-2-carbonyl)-amino]-piperidin-1-yl}-pentanecarboxylate

(33) ethyl 2-methyl-2-(4-fluoro-phenyl)-5-{4-[(4'-trifluoromethyl-biphenyl-2-carbonyl)-amino]-piperidin-1-yl}-pentanecarboxylate

(34) propyl 2-methyl-2-(4-fluoro-phenyl)-5-{4-[(4'-trifluoromethyl-biphenyl-2-carbonyl)-amino]-piperidin-1-yl}-pentanecarboxylate

(35) isopropyl 2-methyl-2-(4-fluoro-phenyl)-5-{4-[(4'-trifluoromethyl-biphenyl-2-carbonyl)-amino]-piperidin-1-yl}-pentanecarboxylate

(36) tert.butyl 2-methyl-2-(4-fluoro-phenyl)-5-{4-[(4'-trifluoromethyl-biphenyl-2-carbonyl)-amino]-piperidin-1-yl}-pentanecarboxylate

(37) methyl 2-methyl-2-phenyl-5-{4-[(4'-methyl-biphenyl-2-carbonyl)-amino]-piperidin-1-yl}-pentanecarboxylate

(38) ethyl 2-methyl-2-phenyl-5-{(4-[(4'-methyl-biphenyl-2-carbonyl)-amino]-piperidin-1-yl}-pentanecarboxylate

(39) propyl 2-methyl-2-phenyl-5-{4-1-[(4'-methyl-biphenyl-2-carbonyl)-amino]-piperidin-1-yl}-pentanecarboxylate

(40) isopropyl 2-methyl-2-phenyl-5-{4-[(4'-methyl-biphenyl-2-carbonyl)-amino]-piperidin-1-yl}-pentanecarboxylate

(41) tert.butyl 2-methyl-2-phenyl-5-{4-[(4'-methyl-biphenyl-2-carbonyl)-amino]-piperidin-1-yl}-pentanecarboxylate

(42) methyl 2-methyl-2-phenyl-5-{4-[(4'-ethyl-biphenyl-2-carbonyl)-amino]-piperidin-1-yl}-pentanecarboxylate

(43) ethyl 2-methyl-2-phenyl-5-{4-[(4'-ethyl-biphenyl-2-carbonyl)-amino]-piperidin-1-yl}-pentanecarboxylate

(44) propyl 2-methyl-2-phenyl-5-{4-[(4'-ethyl-biphenyl-2-carbonyl)-amino]-piperidin-1-yl}-pentanecarboxylate

(45) isopropyl 2-methyl-2-phenyl-5-{4-[(4'-ethyl-biphenyl-2-carbonyl)-amino]-piperidin-1-yl}-pentanecarboxylate

(46) tert.butyl 2-methyl-2-phenyl-5-{4-[(4'-ethyl-biphenyl-2-carbonyl)-amino]-piperidin-1-yl}-pentanecarboxylate

(47) methyl 2-methyl-2-phenyl-5-{4-[(4'-fluoro-biphenyl-2-carbonyl)-amino]-piperidin-1-yl}-pentanecarboxylate

(48) ethyl 2-methyl-2-phenyl-5-{4-[(4'-fluoro-biphenyl-2-carbonyl)-amino]-piperidin-1-yl}-pentanecarboxylate

(49) propyl 2-methyl-2-phenyl-5-{4-[(4'-fluoro-biphenyl-2-carbonyl)-amino]-piperidin-1-yl}-pentanecarboxylate

(50) isopropyl 2-methyl-2-phenyl-5-{4-[(4'-fluoro-biphenyl-2-carbonyl)-amino]-piperidin-1-yl}-pentanecarboxylate

(51) tert.butyl 2-methyl-2-phenyl-5-{4-[(4'-fluoro-biphenyl-2-carbonyl)-amino]-piperidin-1-yl}-pentanecarboxylate

(52) methyl 2-methyl-2-phenyl-5-{4-[(4'-chloro-biphenyl-2-carbonyl)-amino]-piperidin-1-yl}-pentanecarboxylate

(53) ethyl 2-methyl-2-phenyl-5-{4-[(4'-chloro-biphenyl-2-carbonyl)-amino]-piperidin-1-yl}-pentanecarboxylate

(54) propyl 2-methyl-2-phenyl-5-{4-[(4'-chloro-biphenyl-2-carbonyl)-amino]-piperidin-1-yl}-pentanecarboxylate

(55) isopropyl 2-methyl-2-phenyl-5-{4-[(4'-chloro-biphenyl-2-carbonyl)-amino]-piperidin-1-yl}-pentanecarboxylate

(56) tert.butyl 2-methyl-2-phenyl-5-{4-[(4'-chloro-biphenyl-2-carbonyl)-amino]-piperidin-1-yl}-pentanecarboxylate

(57) methyl 2-methyl-2-phenyl-5-{4-[(4'-bromo-biphenyl-2-carbonyl)-amino]-piperidin-1-yl}-pentanecarboxylate

(58) ethyl 2-methyl-2-phenyl-5-{4-[(4'-bromo-biphenyl-2-carbonyl)-amino]-piperidin-yl}-pentanecarboxylate

(59) propyl 2-methyl-2-phenyl-5-{4-[(4'-bromo-biphenyl-2-carbonyl)-amino]-piperidin-1-yl}-pentanecarboxylate

(60) isopropyl 2-methyl-2-phenyl-5-{4-[(4'-bromo-biphenyl-2-carbonyl)-amino]-piperidin-1-yl}-pentanecarboxylate

(61) tert.butyl 2-methyl-2-phenyl-5-{4-[(4'-bromo-biphenyl-2-carbonyl)-amino]-piperidin-1-yl}-pentanecarboxylate

(62) methyl 2-methyl-2-phenyl-5-{4-[(4'-methoxy-biphenyl-2-carbonyl)-amino]-piperidin-1-yl}-pentanecarboxylate

(63) ethyl 2-methyl-2-phenyl-5-{4-[(4'-methoxy-biphenyl-2-carbonyl)-amino]-piperidin-1-yl}-pentanecarboxylate

(64) propyl 2-methyl-2-phenyl-5-{4-[(4'-methoxy-biphenyl-2-carbonyl)-amino]-piperidin-1-yl}-pentanecarboxylate

(65) isopropyl 2-methyl-2-phenyl-5-{4-[(4'-methoxy-biphenyl-2-carbonyl)-amino]-piperidin-1-yl}-pentanecarboxylate

(66) tert.butyl 2-methyl-2-phenyl-5-{4-[(4'-methoxy-biphenyl-2-carbonyl)-amino]-piperidin-1-yl}-pentanecarboxylate

(67) methyl 2-methyl-2-phenyl-5-{4-[(3'-methyl-biphenyl-2-carbonyl)-amino]-piperidin-1-yl}-pentanecarboxylate

(68) ethyl 2-methyl-2-phenyl-5-{4-[(3'-methyl-biphenyl-2-carbonyl)-amino]-piperidin-1-yl}-pentanecarboxylate

(69) propyl 2-methyl-2-phenyl-5-{4-[(3'-methyl-biphenyl-2-carbonyl)-amino]-piperidin-1-yl}-pentanecarboxylate

(70) isopropyl 2-methyl-2-phenyl-5-{4-[(3'-methyl-biphenyl-2-carbonyl)-amino]-piperidin-1-yl}-pentanecarboxylate

(71) tert.butyl 2-methyl-2-phenyl-5-{4-[(3'-methyl-biphenyl-2-carbonyl)-amino]-piperidin-1-yl}-pentanecarboxylate

(72) methyl 2-methyl-2-phenyl-5-{4-[(3'-fluoro-biphenyl-2-carbonyl)-amino]-piperidin-1-yl}-pentanecarboxylate

(73) ethyl 2-methyl-2-phenyl-5-{4-[(3'-fluoro-biphenyl-2-carbonyl)-amino]-piperidin-1-yl}-pentanecarboxylate

(74) propyl 2-methyl-2-phenyl-5-{4-[(3'-fluoro-biphenyl-2-carbonyl)-amino]-piperidin-1-yl}-pentanecarboxylate

(75) isopropyl 2-methyl-2-phenyl-5-{4-[(3'-fluoro-biphenyl-2-carbonyl)-amino]-piperidin-1-yl}-pentanecarboxylate

(76) tert.butyl 2-methyl-2-phenyl-5-{4-[(3'-fluoro-biphenyl-2-carbonyl)-amino]-piperidin-1-yl}-pentanecarboxylate

(77) methyl 2-methyl-2-phenyl-5-{4-[(3'-chloro-biphenyl-2-carbonyl)-amino]-piperidin-1-yl}-pentanecarboxylate

(78) ethyl 2-methyl-2-phenyl-5-{4-[(3'-chloro-biphenyl-2-carbonyl)-amino]-piperidin-1-yl}-pentanecarboxylate

(79) propyl 2-methyl-2-phenyl-5-{4-[(3'-chloro-biphenyl-2-carbonyl)-amino]-piperidin-1-yl}-pentanecarboxylate

(80) isopropyl 2-methyl-2-phenyl-5-{4-[(3'-chloro-biphenyl-2-carbonyl)-amino]-piperidin-1-yl}-pentanecarboxylate

(81) tert.butyl 2-methyl-2-phenyl-5-{4-[(3'-chloro-biphenyl-2-carbonyl)-amino]-piperidin-1-yl}-pentanecarboxylate

(82) methyl 2-methyl-2-phenyl-5-{4-[(4,4'-dichloro-biphenyl-2-carbonyl)-amino]-piperidin-1-yl}-pentanecarboxylate

(83) ethyl 2-methyl-2-phenyl-5-{4-[(4,4'-dichloro-biphenyl-2-carbonyl)-amino]-piperidin-1-yl}-pentanecarboxylate

(84) propyl 2-methyl-2-phenyl-5-{4-[(4,4'-dichloro-biphenyl-2-carbonyl)-amino]-piperidin-1-yl}-pentanecarboxylate

(85) isopropyl 2-methyl-2-phenyl-5-{4-[(4,4'-dichloro-biphenyl-2-carbonyl)-amino]-piperidin-1-yl}-pentanecarboxylate

(86) tert.butyl 2-methyl-2-phenyl-5-{4-[(4,4'-dichloro-biphenyl-2-carbonyl)-amino]-piperidin-1-yl}-pentanecarboxylate

EXAMPLE 2

Methyl 2-ethyl-2-phenyl-5-{4-[(4'-trifluoromethyl-biphenyl-2-carbonyl)-amino]-piperidin-1-yl}-pentanecarboxylate a. methyl 2-phenylbutanecarboxylate 15 g (0.091 mol) of 2-phenylbutane carboxylic acid are dissolved in 150 ml of methanolic hydrochloric acid and stirred for 18 hours at ambient temperature. The solvent is removed and the residue extracted with ethyl acetate and saturated sodium hydrogen carbonate solution. The organic phases are extracted with water and saturated saline solution, dried over magnesium sulphate and concentrated by evaporation.

Yield: 14.4 g (88.8% of theory), $C_{11}H_{14}O_2$ (M=178.23) Calc.: molar peak $(M+Na)^+=201$ Found: molar peak $(M+Na)^+=201$ b. methyl 5-bromo-2-ethyl-2-phenyl-pentanecarboxylate 15 g (0.081 mol) of n-butyl lithium as a 2.5-molar solution in hexane are added dropwise to a solution of 11.35 ml (0.081 mol) of diisopropylamine in 200 ml of anhydrous tetrahydrofuran at −30° C. and stirred for 10 minutes at −10° C. 14.4 g (0.081 mol) of methyl 2-phenylbutanecarboxylate are added dropwise at −76° C. and stirred for 30 minutes at this temperature. Then 8.62 ml (0.085 mol) of 1,3-dibromopropane are added, when the addition has ended the cooling bath is removed and the mixture is stirred for 14 hours at ambient temperature. The reaction solution is poured onto 1.2 l of water and extracted with diethylether. The organic phases are extracted with water, dried over sodium sulphate and the solvent is eliminated. The residue is distilled under high vacuum.

Yield: 10.1 g (41.7% of theory), Boiling point: 127° C. at 0.22 mmbar c. methyl 2-ethyl-2-phenyl-5-{4-[(4'-trifluoromethyl-biphenyl-2-carbonyl)-amino]-piperidin-1-yl1}-pentanecarboxylate 0.2 g (0.574 mmol) of 4'-trifluoromethyl-biphenyl-2-carboxylic acid-piperidin-4-yl-amide, 0.15 g (0.5 mmol) of methyl 5-bromo-2-ethyl-2-phenyl-pentanecarboxylate and 0.083 g (0.6 mmol) of potassium carbonate are dissolved in 10 ml of acetonitrile. The mixture is stirred for 8 hours at 60° C. and for 14 hours at ambient temperature. Then the reaction mixture is poured onto water and extracted with ethyl acetate. The organic phase is dried over sodium sulphate and the solvent is distilled off in the rotary evaporator. After column chromatography on silica gel (eluant: dichloromethane/methanol=20:1) colourless crystals remain.

Yield: 0.172 g (52.9% of theory), $C_{33}H_{37}F_3N_2O_3$ (M=566.67) Melting point: 135° C. Calc.: molar peak $(M+H)^+=567$ Found: molar peak $(M+H)^+=567$ The following compounds may be prepared analogously to Example 2:

(1) ethyl 2-ethyl-2-phenyl-5-{4-[(4'-trifluoromethyl-biphenyl-2-carbonyl)-amino]-piperidin-1-yl}-pentanecarboxylate Prepared from 4'-trifluoromethyl-biphenyl-2-carboxylic acid-piperidin-4-ylamide and ethyl 5-bromo-2-ethyl-2-phenyl-pentanecarboxylate.

Yield: 0.052 g (6% of theory), $C_{34}H_{39}F_3N_2O_3$ (580.69) Melting point: 110° C. Calc.: molar peak $(M+H)^+=581$ Found: molar peak $(M+H)^+=581$ (2) propyl 2-ethyl-2-phenyl-5-{4-[(4'-trifluoromethyl-biphenyl-2-carbonyl)-amino]-piperidin-1-yl}-pentanecarboxylate (3) butyl 2-ethyl-2-phenyl-5-{4-[(4'-trifluoromethyl-biphenyl-2-carbonyl)-amino]-piperidin-1-yl}-pentanecarboxylate (4) pentyl 2-ethyl-2-phenyl-5-{4-[(4'-trifluoromethyl-biphenyl-2-carbonyl)-amino]-piperidin-1-yl}-pentanecarboxylate (5) hexyl 2-ethyl-2-phenyl-5-{4-[(4'-trifluoromethyl-biphenyl-2-carbonyl)-amino]-piperidin-1-yl}-pentanecarboxylate (6) isopropyl 2-ethyl-2-phenyl-5-{4-[(4'-trifluoromethyl-biphenyl-2-carbonyl)-amino]-piperidin-1-yl}-pentanecarboxylate Prepared from 4'-trifluoromethyl-biphenyl-2-carboxylic acid-piperidin-4-ylamide and isopropyl 5-bromo-2-ethyl-2-phenyl-pentanecarboxylate.

Yield: 0.153 g (16.8% of theory), $C_{35}H_{41}F_3N_2O_3$ (594.072) Melting point: 124–125° C. Calc.: molar peak $(M+H)^+=595$ Found: molar peak $(M+H)^+=595$ (7) tert.butyl 2-ethyl-2-phenyl-5-{4-[(4'-trifluoromethyl-biphenyl-2-carbonyl)-amino]-piperidin-1-yl}-pentanecarboxylate (8) isobutyl 2-ethyl-2-phenyl-5-{4-[(4'-trifluoromethyl-biphenyl-2-carbonyl)-amino]-piperidin-1-yl}-pentanecarboxylate (9) sec.butyl 2-ethyl-2-phenyl-5-{4-[(4'-trifluoromethyl-biphenyl-2-carbonyl)-amino]-piperidin-1-yl}-pentanecarboxylate

(10) cyclopropyl 2-ethyl-2-phenyl-5-{4-[(4'-trifluoromethyl-biphenyl-2-carbonyl)-amino]-piperidin-1-yl}-pentanecarboxylate

(11) cyclobutyl 2-ethyl-2-phenyl-5-{4-[(4'-trifluoromethyl-biphenyl-2-carbonyl)-amino]-piperidin-1-yl}-pentanecarboxylate

(12) cyclopentyl 2-ethyl-2-phenyl-5-{4-[(4'-trifluoromethyl-biphenyl-2-carbonyl)-amino]-piperidin-1-yl}-pentanecarboxylate

(13) cyclohexyl 2-ethyl-2-phenyl-5-{4-[(4'-trifluoromethyl-biphenyl-2-carbonyl)-amino]-piperidin-1-yl}-pentanecarboxylate

(14) cycloheptyl 2-ethyl-2-phenyl-5-{4-[(4'-trifluoromethyl-biphenyl-2-carbonyl)-amino]-piperidin-1-yl}-pentanecarboxylate

(15) 2-hydroxyethyl 2-ethyl-2-phenyl-5-{4-[(4'-trifluoromethyl-biphenyl-2-carbonyl)-amino]-piperidin-1-yl}-pentanecarboxylate

(16) 3-hydroxypropyl 2-ethyl-2-phenyl-5-{4-[(4'-trifluoromethyl-biphenyl-2-carbonyl)-amino]-piperidin-1-yl}-pentanecarboxylate

(17) 2-methoxyethyl 2-ethyl-2-phenyl-5-{4-[(4'-trifluoromethyl-biphenyl-2-carbonyl)-amino]-piperidin-1-yl}-pentanecarboxylate

(18) 2-ethoxy-ethyl 2-ethyl-2-phenyl-5-{4-[(4'-trifluoromethyl-biphenyl-2-carbonyl)-amino]-piperidin-1-yl}-pentanecarboxylate

(19) 3-methoxypropyl 2-ethyl-2-phenyl-5-{4-[(4'-trifluoromethyl-biphenyl-2-carbonyl)-amino]-piperidin-1-yl}-pentanecarboxylate

(20) 3-ethoxy-propyl 2-ethyl-2-phenyl-5-{4-[(4'-trifluoromethyl-biphenyl-2-carbonyl)-amino]-piperidin-1-yl}-pentanecarboxylate

(21) 2-amino-ethyl 2-ethyl-2-phenyl-1-5-{4-[(4'-trifluoromethyl-biphenyl-2-carbonyl)-amino]-piperidin-1-yl}-pentanecarboxylate

(22) 3-amino-propyl 2-ethyl-2-phenyl-5-{4-[(4'-trifluoromethyl-biphenyl-2-carbonyl)-amino]-piperidin-1-yl}-pentanecarboxylate

(23) 2-methylaminoethyl 2-ethyl-2-phenyl-5-{4-[(4'-trifluoromethyl-biphenyl-2-carbonyl)-amino]-piperidin-1-yl}-pentanecarboxylate

(24) 3-methylaminopropyl 2-ethyl-2-phenyl-5-{4-[(4'-trifluoromethyl-biphenyl-2-carbonyl)-amino]-piperidin-1-yl}-pentanecarboxylate

(25) 2-dimethylaminoethyl 2-ethyl-2-phenyl-5-{4-[(4'-trifluoromethyl-biphenyl-2-carbonyl)-amino]-piperidin-1-yl}-pentanecarboxylate

(26) 3-dimethylaminopropyl 2-ethyl-2-phenyl-5-{4-[(4'-trifluoromethyl-biphenyl-2-carbonyl)-amino]-piperidin-1-yl}-pentanecarboxylate

(27) benzyl 2-ethyl-2-phenyl-5-{4-[(4'-trifluoromethyl-biphenyl-2-carbonyl)-amino]-piperidin-1-yl}-pentanecarboxylate

(28) pyridin-2-yl-methyl 2-ethyl-2-phenyl-5-{4-[(4'-trifluoromethyl-biphenyl-2-carbonyl)-amino]-piperidin-1-yl}-pentanecarboxylate

(29) pyridin-3-yl-methyl 2-ethyl-2-phenyl-5-{4-[(4'-trifluoromethyl-biphenyl-2-carbonyl)-amino]-piperidin-1-yl}-pentanecarboxylate

(30) pyridin-4-yl-methyl 2-ethyl-2-phenyl-5-{4-[(4'-trifluoromethyl-biphenyl-2-carbonyl)-amino]-piperidin-1-yl}-pentanecarboxylate

(31) pyrimidin-4-yl-methyl 2-ethyl-2-phenyl-5-{4-[(4'-trifluoromethyl-biphenyl-2-carbonyl)-amino]-piperidin-1-yl}-pentanecarboxylate

(32) methyl 2-ethyl-2-(4-fluoro-phenyl)-5-{4-[(4'-trifluoromethyl-biphenyl-2-carbonyl)-amino]-piperidin-1-yl}-pentanecarboxylate

(33) ethyl 2-ethyl-2-(4-fluoro-phenyl)-5-{4-[(4'-trifluoromethyl-biphenyl-2-carbonyl)-amino]-piperidin-1-yl}-pentanecarboxylate

(34) propyl 2-ethyl-2-(4-fluoro-phenyl)-5-{4-[(4'-trifluoromethyl-biphenyl-2-carbonyl)-amino]-piperidin-1-yl}-pentanecarboxylate

(35) isopropyl 2-ethyl-2-(4-fluoro-phenyl)-5-{4-[(4'-trifluoromethyl-biphenyl-2-carbonyl)-amino]-piperidin-1-yl}-pentanecarboxylate

(36) tert.butyl 2-ethyl-2-(4-fluoro-phenyl)-5-{4-[(4'-trifluoromethyl-biphenyl-2-carbonyl)-amino]-piperidin-1-yl}-pentanecarboxylate

(37) methyl 2,2-diphenyl-6-{4-[(4'-trifluoromethyl-biphenyl-2-carbonyl)-amino]-piperidin-1-yl}-pentanecarboxylate

(38) ethyl 2,2-diphenyl-6-{4-[(4'-trifluoromethyl-biphenyl-2-carbonyl)-amino]-piperidin-1-yl}-pentanecarboxylate

(39) propyl 2,2-diphenyl-6-{4-[(4'-trifluoromethyl-biphenyl-2-carbonyl)-amino]-piperidin-1-yl}-pentanecarboxylate

(40) isopropyl 2,2-diphenyl-6-{4-[(4'-trifluoromethyl-biphenyl-2-carbonyl)-amino]-piperidin-1-yl}-pentanecarboxylate

(41) tert.butyl 2,2-diphenyl-6-{4-[(4'-trifluoromethyl-biphenyl-2-carbonyl)-amino]-piperidin-1-yl}-pentanecarboxylate

(42) methyl 2-ethyl-2-phenyl-5-{4-[(4'-methyl-biphenyl-2-carbonyl)-amino]-piperidin-1-yl}-pentanecarboxylate-hydrobromide Prepared from 4'-methyl-biphenyl-2-carboxylic acid-piperidin-4-ylamide and methyl 5-bromo-2-ethyl-2-phenyl-pentanecarboxylate.

Yield: 0.49 g (61% of theory), $C_{33}H_{40}N_2O_3$ (593.61) Melting point: 160° C. Calc.: molar peak $(M+H)^+=513$ Found: molar peak $(M+H)^+=513$

(43) ethyl 2-ethyl-2-phenyl-5-{4-[(4'-methyl-biphenyl-2-carbonyl)-amino]-piperidin-1-yl}-pentanecarboxylate

(44) propyl 2-ethyl-2-phenyl-5-{4-[(4'-methyl-biphenyl-2-carbonyl)-amino]-piperidin-1-yl}-pentanecarboxylate

(45) isopropyl 2-ethyl-2-phenyl-5-{4-[(4'-methyl-biphenyl-2-carbonyl)-amino]-piperidin-1-yl}-pentanecarboxylate

(46) tert.butyl 2-ethyl-2-phenyl-5-{4-[(4'-methyl-biphenyl-2-carbonyl)-amino]-piperidin-1-yl}-pentanecarboxylate

(47) methyl 2-ethyl-2-phenyl-5-{4-[(4'-ethyl-biphenyl-2-carbonyl)-amino]-piperidin-1-yl}-pentanecarboxylate

(48) ethyl 2-ethyl-2-phenyl-5-{4-[(4'-ethyl-biphenyl-2-carbonyl)-amino]-piperidin-1-yl}pentanecarboxylate

(49) propyl 2-ethyl-2-phenyl-5-{4-[(4'-ethyl-biphenyl-2-carbonyl)-amino]-piperidin-1-yl}-pentanecarboxylate

(50) isopropyl 2-ethyl-2-phenyl-5-{4-[(4'-ethyl-biphenyl-2-carbonyl)-amino]-piperidin-1-yl}-pentanecarboxylate

(51) tert.butyl 2-ethyl-2-phenyl-5-{4-[(4'-ethyl-biphenyl-2-carbonyl)-amino]-piperidin-1-yl}-pentanecarboxylate

(52) methyl 2-ethyl-2-phenyl-5-{4-[(4'-fluoro-biphenyl-2-carbonyl)-amino]-piperidin-1-yl}-pentanecarboxylate

(53) ethyl 2-ethyl-2-phenyl-5-{4-[(4'-fluoro-biphenyl-2-carbonyl)-amino]-piperidin-1-yl}-pentanecarboxylate

(54) propyl 2-ethyl-2-phenyl-5-{4-[(4'-fluoro-biphenyl-2-carbonyl)-amino]-piperidin-1-yl}-pentanecarboxylate

(55) isopropyl 2-ethyl-2-phenyl-5-{4-[(4'-fluoro-biphenyl-2-carbonyl)-amino]-piperidin-1-yl}-pentanecarboxylate

(56) tert.butyl 2-ethyl-2-phenyl-5-{4-[(4'-fluoro-biphenyl-2-carbonyl)-amino]-piperidin-1-yl}-pentanecarboxylate

(57) methyl 2-ethyl-2-phenyl-5-{4-[(4'-chloro-biphenyl-2-carbonyl)-amino]-piperidin-1-yl}-pentanecarboxylate

(58) ethyl 2-ethyl-2-phenyl-5-{4-[(4'-chloro-biphenyl-2-carbonyl)-amino]-piperidin-1-yl}-pentanecarboxylate

(59) propyl 2-ethyl-2-phenyl-5-{4-[(4'-chloro-biphenyl-2-carbonyl)-amino]-piperidin-1-yl}-pentanecarboxylate

(60) isopropyl 2-ethyl-2-phenyl-5-{4-[(4'-chloro-biphenyl-2-carbonyl)-amino]-piperidin-1-yl}-pentanecarboxylate

(61) tert.butyl 2-ethyl-2-phenyl-5-{4-[(4'-chloro-biphenyl-2-carbonyl)-amino]-piperidin-1-yl}-pentanecarboxylate

(62) methyl 2-ethyl-2-phenyl-5-{4-[(4'-bromo-biphenyl-2-carbonyl)-amino]-piperidin-1-yl}-pentanecarboxylate

(63) ethyl 2-ethyl-2-phenyl-5-{4-[(4'-bromo-biphenyl-2-carbonyl)-amino]-piperidin-1-yl}-pentanecarboxylate

(64) propyl 2-ethyl-2-phenyl-5-{4-[(4'-bromo-biphenyl-2-carbonyl)-amino]-piperidin-1-yl}-pentanecarboxylate

(65) isopropyl 2-ethyl-2-phenyl-5-{4-[(4'-bromo-biphenyl-2-carbonyl)-amino]-piperidin-1-yl}-pentanecarboxylate

(66) tert.butyl 2-ethyl-2-phenyl-5-{4-[(4'-bromo-biphenyl-2-carbonyl)-amino]-piperidin-1-yl}-pentanecarboxylate

(67) methyl 2-ethyl-2-phenyl-5-{4-[(4'-methoxy-biphenyl-2-carbonyl)-amino]-piperidin-1-yl}-pentanecarboxylate

(68) ethyl 2-ethyl-2-phenyl-5-{4-[(4'-methoxy-biphenyl-2-carbonyl)-amino]-piperidin-1-yl}-pentanecarboxylate

(69) propyl 2-ethyl-2-phenyl-5-{4-[(4'-methoxy-biphenyl-2-carbonyl)-amino]-piperidin-1-yl}-pentanecarboxylate

(70) isopropyl 2-ethyl-2-phenyl-5-{4-[(4'-methoxy-biphenyl-2-carbonyl)-amino]-piperidin-1-yl}-pentanecarboxylate

(71) 2 tert.butyl-ethyl-2-phenyl-5-{4-[(4'-methoxy-biphenyl-2-carbonyl)-amino]-piperidin-1-yl}-pentanecarboxylate

(72) methyl 2-ethyl-2-phenyl-5-{4-[(3'-methyl-biphenyl-2-carbonyl)-amino]-piperidin-1-yl}-pentanecarboxylate

(73) ethyl 2-ethyl-2-phenyl-5-{4-[(3'-methyl-biphenyl-2-carbonyl)-amino]-piperidin-1-yl}-pentanecarboxylate

(74) propyl 2-ethyl-2-phenyl-5-{4-[(3'-methyl-biphenyl-2-carbonyl)-amino]-piperidin-1-yl}-pentanecarboxylate

(75) isopropyl 2-ethyl-2-phenyl-5-{4-[(3'-methyl-biphenyl-2-carbonyl)-amino]-piperidin-1-yl}-pentanecarboxylate

(76) tert.butyl 2-ethyl-2-phenyl-5-{4-[(3'-methyl-biphenyl-2-carbonyl)-amino]-piperidin-1-yl}-pentanecarboxylate

(77) methyl 2-ethyl-2-phenyl-5-{4-[(3'-fluoro-biphenyl-2-carbonyl)-amino]-piperidin-1-yl}-pentanecarboxylate

(78) ethyl 2-ethyl-2-phenyl-5-{4-[(3'-fluoro-biphenyl-2-carbonyl)-amino]-piperidin-1-yl}-pentanecarboxylate

(79) propyl 2-ethyl-2-phenyl-5-{4-[(3'-fluoro-biphenyl-2-carbonyl)-amino]-piperidin-1-yl}-pentanecarboxylate

(80) isopropyl 2-ethyl-2-phenyl-5-{4-[(3'-fluoro-biphenyl-2-carbonyl)-amino]-piperidin-1-yl}-pentanecarboxylate

(81) tert.butyl 2-ethyl-2-phenyl-5-{4-[(3'-fluoro-biphenyl-2-carbonyl)-amino]-piperidin-1-yl}-pentanecarboxylate

(82) methyl 2-ethyl-2-phenyl-5-{4-[(3'-chloro-biphenyl-2-carbonyl)-amino]-piperidin-1-yl}-pentanecarboxylate

(83) ethyl 2-ethyl-2-phenyl-5-{4-[(3'-chloro-biphenyl-2-carbonyl)-amino]-piperidin-1-yl}-pentanecarboxylate

(84) propyl 2-ethyl-2-phenyl-5-{4-[(3'-chloro-biphenyl-2-carbonyl)-amino]-piperidin-1-yl}-pentanecarboxylate

(85) isopropyl 2-ethyl-2-phenyl-5-{4-[(3'-chloro-biphenyl-2-carbonyl)-amino]-piperidin-1-yl}-pentanecarboxylate

(86) tert.butyl 2-ethyl-2-phenyl-5-{4-[(3'-chloro-biphenyl-2-carbonyl)-amino]-piperidin-1-yl}-pentanecarboxylate

(87) methyl 2-ethyl-2-phenyl-5-{4-[(4,4'-dichloro-biphenyl-2-carbonyl)-amino]-piperidin-1-yl}-pentanecarboxylate

(88) ethyl 2-ethyl-2-phenyl-5-{4-[(4,4'-dichloro-biphenyl-2-carbonyl)-amino]-piperidin-1-yl}-pentanecarboxylate

(89) propyl 2-ethyl-2-phenyl-5-{4-[(4,4'-dichloro-biphenyl-2-carbonyl)-amino]-piperidin-1-yl}-pentanecarboxylate

(90) isopropyl 2-ethyl-2-phenyl-5-{4-[(4,4'-dichloro-biphenyl-2-carbonyl)-amino]-piperidin-1-yl}-pentanecarboxylate

(91) tert.butyl 2-ethyl-2-phenyl-5-{4-[(4,4'-dichloro-biphenyl-2-carbonyl)-amino]-piperidin-1-yl}-pentanecarboxylate

EXAMPLE 3

Methyl2-methyl-2-phenyl-5-{4-[(biphenyl-2-carbonyl)-amino]-piperidin-1-yl}-pentanecarboxylate a. Biphenyl-2-carboxylic acid chloride 1.54 ml (0.018 mol) of oxalyl chloride are added dropwise to a suspension of 3 g (0.015 mol)) of biphenyl-2-carboxylic acid in 100 ml of dichloromethane and 0.3 ml dimethylformamide at 0° C. After the reaction has ended the reaction mixture is concentrated by distillation and the biphenyl-2-carboxylic acid chloride is further reacted as a crude product.

Yield: 3.1 g (95.4% of theory).

b. Biphenyl-2-carboxylic acid-(1-benzyl-piperidin-4-yl)-amide 3 g (0.014 mol) of 4'-trifluoromethyl-biphenyl-2-carboxylic acid chloride, dissolved in 30 ml of dichloromethane, are added dropwise at 15 to –20° C. to a solution of 2.65 ml (0.013 mol) of 4-amino-1-benzyl-piperidine and 6 ml (0.043 mol) of triethylamine in 100 ml of dichloromethane. The mixture is stirred for 14 hours at ambient temperature. The reaction solution is extracted with a mixture of I molar sodium hydrogen carbonate solution and 1N sodium hydroxide solution. The organic phase is dried over sodium sulphate and the solvent is eliminated. The residue is recrystallised from 650 ml of ethanol.

Yield: 2.93 g (56.5% of theory), Melting point: 144–145° C.

c. Biphenyl-2-carboxylic acid-piperidin-4-ylamide-dihydrochloride 3.2 g (0.009 mol) of biphenyl-2-carboxylic acid-(1-benzyl-piperidin-4-yl)-amide are dissolved in 80 ml ethanol, mixed with 0.7 g of palladium hydroxide (20% on charcoal) and stirred for five hours at 50° C. in a Parr apparatus in a hydrogen atmosphere (50 psi). Then the catalyst is filtered off, the residue is evaporated down and dissolved in ethyl acetate. After the addition of ethanolic hydrochloric acid the precipitate is filtered off and dried in a circulating air drier at 100° C.

Yield: 2.4 g (75.5% of theory), Melting point: >250° C. $C_{18}H_{20}N_2O$ (M=281.38) Calc.: molar peak $(M+H)^+=281$ Found: molar peak $(M+H)^+=281$ d. methyl 2-methyl-2-phenyl-5-{4-[(biphenyl-2-carbonyl)-amino]-piperidin-1-yl}-pentanecarboxylate A solution of 0.634 g (0.002 mol) of biphenyl-2-carboxylic acid-piperidin-4-ylamide, 0.5 g (1.75 mmol) of methyl 5-bromo-2-methyl-2-phenyl-pentanecarboxylate and 1 ml (0.007 mol) of triethylamine are dissolved in 3 ml dimethylformamide. The mixture is stirred for 14 hours at 80° C. Then the reaction mixture is poured onto water and extracted with ethyl acetate. The organic phase is dried over sodium sulphate. After column chromatography on silica gel (eluant: dichloromethane/methanol=10:1) colourless crystals remain.

Yield: 0.12 g (12.4% of theory), $C_{31}H_{36}N_2O_3$ (M=484.64) Melting point: 96° C. Calc.: molar peak $(M+H)^+=485$ Found: molar peak $(M+H)^+=485$ The following compounds may be prepared analogously to Example 3:

(1) ethyl 2-methyl-2-phenyl-5-{4-[(biphenyl-2-carbonyl)-amino]-piperidin-1-yl}-pentanecarboxylate (2) propyl 2-methyl-2-phenyl-5-{4-[(biphenyl-2-carbonyl)-amino]-piperidin-1-yl}-pentanecarboxylate (3) isopropyl 2-methyl-2-phenyl-5-{4-[(biphenyl-2-carbonyl)-amino]-piperidin-1-yl}-pentanecarboxylate (4) methyl 2-ethyl-2-phenyl-5-{4-[(biphenyl-2-carbonyl)-amino]-piperidin-1-yl}-pentanecarboxylate (5) ethyl 2-ethyl-2-phenyl-5-{4-[(biphenyl-2-carbonyl)-amino]-piperidin-1-yl}-pentanecarboxylate (6) propyl 2-ethyl-2-phenyl-5-{4-[(biphenyl-2-carbonyl)-amino]-piperidin-1-yl}-pentanecarboxylate (7) isopropyl 2-ethyl-2-phenyl-5-{4-[(biphenyl-2-carbonyl)-amino]-piperidin-1-yl}-pentanecarboxylate

EXAMPLE 4

2-methyl-2-phenyl-5-{4-[(4'-trifluoromethyl-biphenyl-2-carbonyl)-amino]-piperidin-1-yl}-pentanecarboxylic acid A suspension of 1.5 g (0.0027 mol) of methyl 2-methyl-2-phenyl-5-{4-[(4'-trifluoromethyl-biphenyl-2-carbonyl)-amino]-piperidin-1-yl}-pentanecarboxylate in 60 ml of 6N hydrochloric acid is refluxed for 25 hours. After cooling the precipitate is filtered off and washed with water and ethyl acetate.

Yield: 1.1 g (75.8% of theory), $C_{31}H_{33}F_3N_2O_3$ (M=538.61) Melting point: 203–205° C. Calc.: molar peak $(M+H)^+=538$ Found: molar peak $(M+H)^+=538$ The following compounds may be prepared analogously to Example 4:

(1) 2-methyl-2-phenyl-5-{4-[(4'-methyl-biphenyl-2-carbonyl)-amino]-piperidin-1-yl}-pentanecarboxylic acid (2) 2-methyl-2-phenyl-5-{4-[(4'-chloro-biphenyl-2-carbonyl)-amino]-piperidin-1-yl}-pentanecarboxylic acid (3) 2-methyl-2-phenyl-5-{4-[(4'-methoxy-biphenyl-2-carbonyl)-amino]-piperidin-1-yl}-pentanecarboxylic acid (4) 2-ethyl-2-phenyl-5-{4-[(4'-trifluoromethyl-biphenyl-2-carbonyl)-amino]-piperidin-1-yl}-pentanecarboxylic acid (5) 2-ethyl-2-phenyl-5-{4-[(4'-methyl-biphenyl-2-carbonyl)-amino]-piperidin-1-yl}-pentanecarboxylic acid (6) 2-ethyl-2-phenyl-5-{4-[(4'-chloro-biphenyl-2-carbonyl)-amino]-piperidin-1-yl}-pentanecarboxylic acid (7) 2-ethyl-2-phenyl-5-{4-[(4'-methoxy-biphenyl-2-carbonyl)-amino]-piperidin-1-yl}-pentanecarboxylic acid

EXAMPLE 5

Methyl 2-methyl-2-phenyl-5-{4-[(4'-trifluoromethyl-biphenyl-2-carbonyl)-N-methyl-amino]-piperidin-1-yl}-pentanecarboxylate 0.095 g (0.803 mmol) of sodium hydride (55 to 65% in oil) are added to a solution of 0.4 g (0.724 mmol) of methyl 2-methyl-2-phenyl-5-{4-[(4'-trifluoromethyl-biphenyl-2-carbonyl)-amino]-piperidin-1-yl}-pentanecarboxylate in 5 ml of dimethylformamide at ambient temperature and stirred for one hour. Then 0.05 ml (0.803 mmol) of methyl iodide are added and the mixture is stirred for 14 hours. The reaction solution is poured onto water, extracted with ethyl acetate, and the organic phase is dried over sodium sulphate. The product is purified by column chromatography on silica gel (eluant: dichloromethane/methanol=5:1).

Yield: 0.04 g (10% of theory), $C_{33}H_{37}F_3N_2O_3$ (M=566.67) Calc.: molar peak $(M+H)^+=567$ Found: molar peak $(M+H)^+=567$ The following compounds may be prepared analogously to Example 5:

(1) ethyl 2-methyl-2-phenyl-5-{4-[(4'-trifluoromethyl-biphenyl-2-carbonyl)-N-methyl-amino]-piperidin-1-yl}-pentanecarboxylate (2) propyl 2-methyl-2-phenyl-5-{4-[(4'-trifluoromethyl-biphenyl-2-carbonyl)-N-methyl-amino]-piperidin-1-yl}-pentanecarboxylate (3) isopropyl 2-methyl-2-phenyl-5-{4-[(4'-trifluoromethyl-biphenyl-2-carbonyl)-N-methyl-amino]-piperidin-1-yl}-pentanecarboxylate (4) tert.butyl 2-methyl-2-phenyl-5-{4-[(4'-trifluoromethyl-biphenyl-2-carbonyl)-N-methyl-amino]-piperidin-1-yl}-pentanecarboxylate (5) methyl 2-methyl-2-phenyl-5-{4-[(4'-trifluoromethyl-biphenyl-2-carbonyl)-N-ethyl-amino]-piperidin-1-yl}-pentanecarboxylate (6) ethyl 2-methyl-2-phenyl-5-{4-[(4'-trifluoromethyl-biphenyl-2-carbonyl)-N-ethyl-amino]-piperidin-1-yl}-pentanecarboxylate (7) propyl 2-methyl-2-phenyl-5-{4-[(4'-trifluoromethyl-biphenyl-2-carbonyl)-N-ethyl-amino]-piperidin-1-yl}-pentanecarboxylate (8) isopropyl 2-methyl-2-phenyl-5-{4-[(4'-trifluoromethyl-biphenyl-2-carbonyl)-N-ethyl-amino]-piperidin-1-yl}-pentanecarboxylate (9) tert.butyl 2-methyl-2-phenyl-5-{4-[(4'-trifluoromethyl-biphenyl-2-carbonyl)-N-ethyl-amino]-piperidin-1-yl}-pentanecarboxylate

(10) methyl 2-ethyl-2-phenyl-5-{4-[(4'-trifluoromethyl-biphenyl-2-carbonyl)-N-methyl-amino]-piperidin-1-yl}-pentanecarboxylate

(11) ethyl 2-ethyl-2-phenyl-5-{-4-[(4'-trifluoromethyl-biphenyl-2-carbonyl)-N-methyl-amino]-piperidin-1-yl}-pentanecarboxylate

(12) propyl 2-ethyl-2-phenyl-5-{4-[(4'-trifluoromethyl-biphenyl-2-carbonyl)-N-methyl-amino]-piperidin-1-yl}-pentanecarboxylate

(13) isopropyl 2-ethyl-2-phenyl-5-{4-[(4'-trifluoromethyl-biphenyl-2-carbonyl)-N-methyl-amino]-piperidin-1-yl}-pentanecarboxylate

(14) tert.butyl 2-ethyl-2-phenyl-5-{4-[(4'-trifluoromethyl-biphenyl-2-carbonyl)-N-methyl-amino]-piperidin-1-yl}pentanecarboxylate

(15) methyl 2-ethyl-2-phenyl-5-{4-[(4'-trifluoromethyl-biphenyl-2-carbonyl)-N-ethyl-amino]-piperidin-1-yl}-pentanecarboxylate

(16) ethyl 2-ethyl-2-phenyl-5-{4-[(4'-trifluoromethyl-biphenyl-2-carbonyl)-N-ethyl-amino]-piperidin-1-yl}-pentanecarboxylate

(17) propyl 2-ethyl-2-phenyl-5-{4-[(4'-trifluoromethyl-biphenyl-2-carbonyl)-N-ethyl-amino]-piperidin-1-yl}-pentanecarboxylate

(18) isopropyl 2-ethyl-2-phenyl-5-{4-[(4'-trifluoromethyl-biphenyl-2-carbonyl)-N-ethyl-amino]-piperidin-1-yl}-pentanecarboxylate

(19) tert.butyl 2-ethyl-2-phenyl-5-{4-[(4'-trifluoromethyl-biphenyl-2-carbonyl)-N-ethyl-amino]-piperidin-1-yl}-pentanecarboxylate

EXAMPLE 6

Methyl 2-methyl-2-phenyl-6-{4-[(4'-trifluoromethyl-biphenyl-2-carbonyl)-amino]-piperidin-1-yl}-hexanecarboxylate a. methyl 6-bromo-2-ethyl-2-phenyl-hexanecarboxylate 40 ml (0.1 mol) of n-butyl lithium as a 2.5 molar solution in hexane are added dropwise to a solution of 14 ml (0.1 mol) of diisopropylamine in 150 ml of anhydrous tetrahydrofuran at −30° C. and stirred for 10 minutes at −10° C. At −76° C., 16.4 g (0.1 mol) of methyl 2-phenylbutanecarboxylate are added dropwise and the mixture is stirred for 30 minutes at this temperature. Then 12.12 ml (0.101 mol) of 1,3-dibromobutane are added, when the addition has ended the cooling bath is removed and the mixture is stirred for 14 hours at ambient temperature. The reaction solution is poured onto 1.2 l water and extracted with diethylether. The organic phases are extracted with water, dried over sodium sulphate and the solvent is eliminated. The residue is distilled under high vacuum.

Yield: 15.8 g (52.8% of theory), Boiling point: 100–117° C. at 0.17 mmbar $C_{14}H_{19}BrO_2$ (M=299.21) Calc.: molar peak $(M+Na)^+=321/23$ Found: molar peak $(M+Na)^+=321/23$ b. methyl 2-methyl-2-phenyl-6-{4-[(4'-trifluoromethyl-biphenyl-2-carbonyl)-amino]-piperidin-1-yl}-hexanecarboxylate 0.2 g (0.574 mmol) of 4'-trifluoromethyl-biphenyl-2-carboxylic acid-piperidin-4-yl-amide, 0.15 g (0.5 mmol) of methyl 6-bromo-2-methyl-2-phenyl-hexanecarboxylate and 0.083 g (0.6 mmol) of potassium carbonate are dissolved in 10 ml of acetonitrile. The mixture is stirred for 8 hours at 60° C. and for 14 hours at ambient temperature. Then the reaction mixture is poured onto water and extracted with ethyl acetate. The organic phase is dried over sodium sulphate and the solvent is distilled off in the rotary evaporator. After column chromatography on silica gel (eluant: dichloromethane/methanol=20:1) a highly viscous oil remains.

Yield: 0.133 g (40.9% of theory), $C_{33}H_{37}F_3N_2O_3$ (M=566.67) Calc.: molar peak $(M+H)^+=567$ Found: molar peak $(M+H)^+=567$ The following compounds may be prepared analogously to Example 6:

(1) ethyl 2-methyl-2-phenyl-6-{4-[(4'-trifluoromethyl-biphenyl-2-carbonyl)-amino-piperidin-1-yl}-hexanecarboxylate (2) propyl 2-methyl-2-phenyl-6-{4-[(4'-trifluoromethyl-biphenyl-2-carbonyl)-amino-piperidin-1-yl}-hexanecarboxylate (3) isopropyl 2-methyl-2-phenyl-6-{4-[(4'-trifluoromethyl-biphenyl-2-carbonyl)-amino]-piperidin-1-yl}-hexanecarboxylate (4) tert. butyl 2-methyl-2-phenyl-6-{4-[(4'-trifluoromethyl-biphenyl-2-carbonyl)-amino]-piperidin-1-yl}-hexanecarboxylate (5) methyl 2-ethyl-2-phenyl-6-{4-[(4'-trifluoromethyl-biphenyl-2-carbonyl)-amino]-piperidin-1-yl}-hexanecarboxylate (6) ethyl 2-ethyl-2-phenyl-6-{4-[(4'-trifluoromethyl-biphenyl-2-carbonyl)-amino]-piperidin-1-yl}-hexanecarboxylate (7) propyl 2-ethyl-2-phenyl-6-{4-[(4'-trifluoromethyl-biphenyl-2-carbonyl)-amino]-piperidin-1-yl}-hexanecarboxylate (8) isopropyl 2-ethyl-2-phenyl-6-{4-[(4'-trifluoromethyl-biphenyl-2-carbonyl)-amino]-piperidin-1-yl}-hexanecarboxylate (9) tert. butyl 2-ethyl-2-phenyl-6-{4-[(4'-trifluoromethyl-biphenyl-2-carbonyl)-amino]-piperidin-1-yl}-hexanecarboxylate

(10) methyl 2-methyl-2-phenyl-4-{4-[(4'-trifluoromethyl-biphenyl-2-carbonyl)-amino]-piperidin-1-yl}-butanecarboxylate

(11) ethyl 2-methyl-2-phenyl-4-{4-[(4'-trifluoromethyl-biphenyl-2-carbonyl)-amino]-piperidin-1-yl}-butanecarboxylate

(12) propyl 2-methyl-2-phenyl-4-{4-[(4'-trifluoromethyl-biphenyl-2-carbonyl)-amino]-piperidin-1-yl}-butanecarboxylate

(13) isopropyl 2-methyl-2-phenyl-4-{4-[(4'-trifluoromethyl-biphenyl-2-carbonyl)-amino]-piperidin-1-yl}-butanecarboxylate

(14) tert.butyl 2-methyl-2-phenyl-4-{4-[(4'-trifluoromethyl-biphenyl-2-carbonyl)-amino]-piperidin-1-yl}-butanecarboxylate

(15) methyl 2-ethyl-2-phenyl-4-{4-[(4'-trifluoromethyl-biphenyl-2-carbonyl)-amino]-piperidin-1-yl}-butanecarboxylate

(16) ethyl 2-ethyl-2-phenyl-4-{4-[(4'-trifluoromethyl-biphenyl-2-carbonyl)-amino]-piperidin-1-yl}-butanecarboxylate

(17) propyl 2-ethyl-2-phenyl-4-{4-[(4'-trifluoromethyl-biphenyl-2-carbonyl)-amino]-piperidin-1-yl}-butanecarboxylate

(18) isopropyl 2-ethyl-2-phenyl-4-{4-[(4'-trifluoromethyl-biphenyl-2-carbonyl)-amino]-piperidin-1-yl}-butanecarboxylate

(19) tert.butyl 2-ethyl-2-phenyl-4-{4-[(4'-trifluoromethyl-biphenyl-2-carbonyl)-amino]-piperidin-1-yl}-butanecarboxylate

(20) methyl 2-methyl-2-phenyl-3-{4-[(4'-trifluoromethyl-biphenyl-2-carbonyl)-amino]-piperidin-1-yl}-propanecarboxylate

(21) ethyl 2-methyl-2-phenyl-3-{4-[(4'-trifluoromethyl-biphenyl-2-carbonyl)-amino]-piperidin-1-yl}-propanecarboxylate

(22) propyl methyl-2-phenyl-3-{4-[(4'-trifluoromethyl-biphenyl-2-carbonyl)-amino]-piperidin-1-yl}-propanecarboxylate

(23) isopropyl 2-methyl-2-phenyl-3-{4-[(4'-trifluoromethyl-biphenyl-2-carbonyl)-amino]-piperidin-1-yl}-propanecarboxylate

(24) tert.butyl 2-methyl-2-phenyl-3-{4-[(4'-trifluoromethyl-biphenyl-2-carbonyl)-amino]-piperidin-1-yl}-propanecarboxylate

(25) methyl 2-ethyl-2-phenyl-3-{4-[(4'-trifluoromethyl-biphenyl-2-carbonyl)-amino]-piperidin-1-yl}-propanecarboxylate

(26) ethyl 2-ethyl-2-phenyl-3-{4-[(4'-trifluoromethyl-biphenyl-2-carbonyl)-amino]-piperidin-1-yl}-propanecarboxylate

(27) propyl 2-ethyl-2-phenyl-3-{4-[(4'-trifluoromethyl-biphenyl-2-carbonyl)-amino]-piperidin-1-yl}-propanecarboxylate

(28) isopropyl 2-ethyl-2-phenyl-3-{4-[(4'-trifluoromethyl-biphenyl-2-carbonyl)-amino]-piperidin-1-yl}-propanecarboxylate

(29) tert.butyl 2-ethyl-2-phenyl-3-{4-[(4'-trifluoromethyl-biphenyl-2-carbonyl)-amino]-piperidin-1-yl}-propanecarboxylate

EXAMPLE 7

Tablets Containing 5 mg of Active Substance per Tablet

| Composition: | |
|---|---|
| active substance | 5.0 mg |
| lactose monohydrate | 70.8 mg |
| microcrystalline cellulose | 40.0 mg |
| sodium carboxymethylcellulose, insolubly crosslinked | 3.0 mg |
| magnesium stearate | 1.2 mg |

Preparation:

The active substance is mixed for 15 minutes with lactose monohydrate, microcrystalline cellulose and sodium carboxymethylcellulose in a suitable diffusion mixer. Magnesium stearate is added and mixed with the other substances for another 3 minutes.

The finished mixture is compressed in a tablet press to form facetted flat round tablets.

Diameter of the tablet: 7 mm
Weight of a tablet: 120 mg

EXAMPLE 8

Capsules Containing 50 mg of Active Substance per Capsule

| Composition: | |
|---|---|
| active substance | 50.0 mg |
| lactose monohydrate | 130.0 mg |
| corn starch | 65.0 mg |
| highly dispersed silicon dioxide | 2.5 mg |
| magnesium stearate | 2.5 mg |

Preparation:

A starch paste is prepared by swelling some of the corn starch in a suitable amount of hot water. The paste is then left to cool to room temperature.

The active substance is premixed for 15 minutes in a suitable mixer with lactose monohydrate and corn starch. The starch paste is added and the mixture is mixed with sufficient water to produce a moist homogeneous mass. The moist mass is passed through a screen with a mesh size of 1.6 mm. The screened granules are dried on racks at about 55° C. for 12 hours.

The dried granules are then passed through screens with mesh sizes of 1.2 and 0.8 mm. Highly dispersed silica is mixed with the granules in a suitable mixer for 3 minutes. Then magnesium stearate is added and mixing is continued for another 3 minutes.

The finished mixture is packed into empty size 1 hard gelatine capsule shells using a capsule filling machine.

EXAMPLE 9

Tablets Containing 200 mg of Active Substance per Tablet

| Composition: | |
| --- | --- |
| active substance | 200.0 mg |
| lactose-monohydrate | 167.0 mg |
| microcrystalline cellulose | 80.0 mg |
| hydroxypropyl-methylcellulose, type 2910 | 10.0 mg |
| poly-1-vinyl-2-pyrrolidone, insolubly crosslinked | 20.0 mg |
| magnesium stearate | 3.0 mg |

Preparation:

HPMC is dispersed in hot water. After cooling, the mixture yields a clear solution.

The active substance is premixed in a suitable mixer for 5 minutes with lactose monohydrate and microcrystalline cellulose. The HPMC solution is added and the mixing is continued until a homogeneous moist composition is obtained. The moist composition is passed through a screen with a mesh size of 1.6 mm. The screened granules are dried on racks at about 55° C. for 12 hours.

The dried granules are then passed through screens with mesh sizes of 1.2 and 0.8 mm. Poly-1-vinyl-2-pyrrolidone is mixed with the granules in a suitable mixer for 3 minutes. Then magnesium stearate is added and mixing is continued for another 3 minutes.

The finished mixture is compressed in a tablet press to form oblong tablets (16.2×7.9 mm).

Weight of a tablet: 480 mg

What is claimed is:

1. A biphenyl compound of the following formula (I):

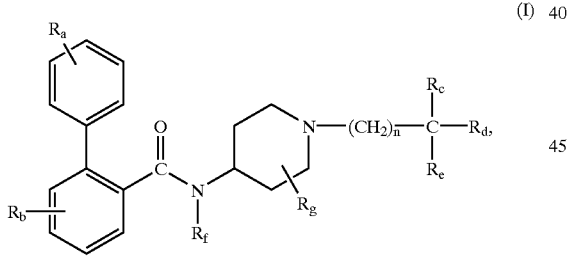

wherein n denotes the number 1, 2, 3, 4 or 5, $R_a$ and $R_b$, which may be identical or different, each denote a hydrogen, fluorine, chlorine or bromine atom, a $C_{1-3}$-alkyl group wherein the hydrogen atoms may be wholly or partially replaced by fluorine atoms, a hydroxy, $C_{1-3}$-alkoxy, amino, $C_{1-3}$-alkylamino or di-($C_{1-3}$-alkyl)-amino group, $R_c$ denotes a hydrogen atom, a $C_{1-10}$-alkyl, $C_{3-7}$-cycloalkyl or $C_{3-7}$-cycloalkyl-$C_{1-3}$-alkyl group, wherein in each case the hydrogen atoms may be wholly or partially replaced by fluorine atoms, a phenyl, naphthyl or monocyclic 5 or 6-membered heteroaryl group optionally substituted by a fluorine, chlorine or bromine atom, by a $C_{1-3}$-alkyl group wherein the hydrogen atoms may be wholly or partially replaced by fluorine atoms, by a hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, by a 3- to 7-membered cycloalkyleneimino group, wherein the methylene group in the 4 position in a 6- or 7-membered cycloalkyleneimino group may additionally be replaced by an oxygen or sulphur atom, by a sulphinyl, sulphonyl, imino or N-($C_{1-3}$-alkyl)-imino group, by a nitro, amino, $C_{1-3}$-alkylamino, di-($C_{1-3}$-alkyl)-amino, $C_{1-3}$-alkylcarbonylamino, N-($C_{1-3}$-alkyl)-$C_{1-3}$-alkylcarbonylamino, $C_{1-3}$-alkylsulphonylamino or N-($C_{1-3}$-alkyl)-$C_{1-3}$-alkylsulphonylamino group, wherein the 6-membered heteroaryl group contains one, two or three nitrogen atoms and the 5-membered heteroaryl group contains an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and optionally a phenyl ring may be fused to the abovementioned monocyclic heterocyclic groups via two adjacent carbon atoms, $R_d$ denotes a phenyl, naphthyl or monocyclic 5 or 6-membered heteroaryl group optionally substituted by a fluorine, chlorine or bromine atom, by a $C_{1-3}$-alkyl group wherein the hydrogen atoms may be wholly or partially replaced by fluorine atoms, by a hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, by a 3- to 7-membered cycloalkyleneimino group, wherein the methylene group may additionally be replaced in the 4 position in a 6- or 7-membered cycloalkyleneimino group by an oxygen or sulphur atom, by a sulphinyl, sulphonyl, imino or N-($C_{1-3}$-alkyl)-imino group, by a nitro, amino, $C_{1-3}$-alkylamino, di-($C_{1-3}$-alkyl)-amino, $C_{1-3}$-alkylcarbonylamino, N-($C_{1-3}$-alkyl)-$C_{1-3}$-alkylcarbonylamino, $C_{1-3}$-alkylsulphonylamino or N-($C_{1-3}$-alkyl)-$C_{1-3}$-alkylsulphonylamino group, wherein the 6-membered heteroaryl group contains one, two or three nitrogen atoms and the 5-membered heteroaryl group contains an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and optionally a phenyl ring may be fused to the abovementioned monocyclic heterocyclic groups via two adjacent carbon atoms, $R_e$ denotes a carboxy group, a $C_{1-6}$-alkoxycarbonyl or $C_{3-7}$-cycloalkoxycarbonyl group wherein the alkyl or cycloalkyl moiety may be substituted in each case from the 2 position, relative to the oxygen atom, by a $C_{1-3}$-alkoxy, amino, $C_{1-3}$-alkylamino or di-($C_{1-3}$-alkyl)-amino group, a phenyl-$C_{1-3}$-alkoxycarbonyl or heteroaryl-$C_{1-3}$-alkoxycarbonyl group, and the heteroaryl moiety is a monocyclic 5 or 6-membered heteroaryl group optionally substituted by a fluorine, chlorine or bromine atom, by a $C_{1-3}$-alkyl group wherein the hydrogen atoms may be wholly or partially replaced by fluorine atoms, by a hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, by a 3- to 7-membered cycloalkyleneimino group, wherein the methylene group may additionally be replaced in the 4 position in a 6- or 7-membered cycloalkyleneimino group by an oxygen or sulphur atom, by a sulphinyl, sulphonyl, imino or N-($C_{1-3}$-alkyl)-imino group, by a nitro, amino, $C_{1-3}$-alkylamino, di-($C_{1-3}$-alkyl)-amino, $C_{1-3}$-alkylcarbonylamino, N-($C_{1-3}$-alkyl)-$C_{1-3}$-alkylcarbonylamino, $C_{1-3}$-alkylsulphonylamino or N-($C_{1-3}$-alkyl)-$C_{1-3}$-alkylsulphonylamino group, wherein the 6-membered heteroaryl group contains one, two or three nitrogen atoms and the 5-membered heteroaryl group contains an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and optionally a phenyl ring may be fused to the abovementioned monocyclic heterocyclic groups via two adjacent carbon atoms, $R_f$ denotes a hydrogen atom, a $C_{1-3}$-alkyl or phenyl-$C_{1-3}$-alkyl group and $R_g$ denotes a hydrogen atom or a $C_{1-3}$-alkyl group, or an isomer or salt thereof.

2. A biphenyl compound of formula I according to claim 1, wherein $R_b$ to $R_g$ are defined as in claim 1 and $R_a$ is in the 3' or 4' position and is as defined in claim 1 with the exception of the hydrogen atom, or an isomer or salt thereof.

3. A biphenyl compound of formula I according to claim 1, wherein n denotes the number 3, 4 or 5, $R_a$ denotes a hydrogen, fluorine, chlorine or bromine atom, a $C_{1-3}$-alkyl, trifluoromethyl or $C_{1-3}$-alkoxy group, $R_b$ denotes a hydrogen, fluorine, chlorine or bromine atom, $R_c$ denotes a $C_{1-5}$-alkyl, $C_{3-7}$-cycloalkyl or $C_{3-7}$-cycloalkyl-$C_{1-3}$-alkyl group or a phenyl group optionally substituted by a fluorine, chlorine or bromine atom or by a $C_{1-3}$-alkyl group, $R_d$ denotes a phenyl group optionally substituted by a fluorine, chlorine or bromine atom or by a $C_{1-3}$-alkyl group, $R_e$ denotes a carboxy group, a $C_{1-6}$-alkoxycarbonyl or $C_{3-7}$-cycloalkoxycarbonyl group wherein the alkyl or cycloalkyl moiety may be substituted in each case from the 2 position, relative to the oxygen atom, by a $C_{1-3}$-alkoxy, amino, $C_{1-3}$-alkylamino or di-($C_{1-3}$-alkyl)-amino group, a phenyl-$C_{1-3}$-alkoxycarbonyl, pyridyl-$C_{1-3}$-alkoxycarbonyl or pyrimidyl-$C_{1-3}$-alkoxycarbonyl group, $R_f$ denotes a hydrogen atom or a $C_{1-3}$-alkyl group and $R_g$ denotes a hydrogen atom or a $C_{1-3}$-alkyl group, or an isomer or salt thereof.

4. A biphenyl compound of formula I according to claim 1 selected from the following compounds:

(a) methyl 2-methyl-2-phenyl-5-{4-[(4'-trifluoromethyl-biphenyl-2-carbonyl)-amino]-piperidin-1-yl}-pentanecarboxylate, (b) methyl 2-ethyl-2-phenyl-5-{4-[(4'-trifluoromethyl-biphenyl-2-carbonyl)-amino]-piperidin-1-yl}-pentanecarboxylate and (c) methyl 2-methyl-2-phenyl-6-{4-[(4'-trifluoromethyl-biphenyl-2-carbonyl)-amino]-piperidin-1-yl}-hexanecarboxylate.

5. A physiologically acceptable salt of a compound according to claim 1.

6. A pharmaceutical composition comprising a compound according to claim 1, or a physiologically acceptable salt thereof, optionally together with one or more inert carriers and/or diluents.

7. A method of lowering the plasma levels of atherogenic lipoproteins in a patient in need thereof comprising administering to said patient a therapeutically effective amount of a compound according to claim 1.

8. A method for treating hyperlipidaemia, atherosclerosis or the clinical sequelae thereof, diabetes mellitus, adiposity or pancreatitis in a patient in need thereof comprising administering to said patient a therapeutically effective amount of a compound according to claim 1.

* * * * *